United States Patent
Aoki et al.

(10) Patent No.: US 12,180,455 B2
(45) Date of Patent: Dec. 31, 2024

(54) CULTURE DEVICE

(71) Applicant: PHC CORPORATION, Ehime (JP)

(72) Inventors: Hikaru Aoki, Gunma (JP); Hiroki Hirai, Kagawa (JP); Manami Baba, Gunma (JP)

(73) Assignee: PHC CORPORATION, Ehime (JP)

( * ) Notice: Subject to any disclaimer, the term of this patent is extended or adjusted under 35 U.S.C. 154(b) by 926 days.

(21) Appl. No.: 17/189,184

(22) Filed: Mar. 1, 2021

(65) Prior Publication Data
US 2021/0180002 A1 Jun. 17, 2021

Related U.S. Application Data

(63) Continuation of application No. PCT/JP2019/031921, filed on Aug. 14, 2019.

(30) Foreign Application Priority Data

Sep. 6, 2018 (JP) .................... 2018-166647

(51) Int. Cl.
| C12M 3/00 | (2006.01) |
| C12M 1/00 | (2006.01) |
| C12M 1/12 | (2006.01) |
| C12M 1/34 | (2006.01) |

(52) U.S. Cl.
CPC ............ *C12M 41/32* (2013.01); *C12M 1/005* (2013.01); *C12M 23/48* (2013.01); *C12M 37/00* (2013.01); *C12M 41/14* (2013.01); *C12M 1/121* (2013.01)

(58) Field of Classification Search
USPC ..................................... 435/303.1
See application file for complete search history.

(56) References Cited

U.S. PATENT DOCUMENTS

2019/0024036 A1   1/2019  Hitomi et al.

FOREIGN PATENT DOCUMENTS

| CN | 103477168 A | 12/2013 |
| EP | 0 990 699 A1 | 4/2000 |
| JP | 2010-007870 A | 1/2010 |
| JP | 2010-017151 A | 1/2010 |

(Continued)

OTHER PUBLICATIONS

Extended European Search Report dated Sep. 9, 2021 issued in corresponding European Patent Application No. 19857531.8.

(Continued)

*Primary Examiner* — Holly Kipouros
*Assistant Examiner* — Nathan G Esperon
(74) *Attorney, Agent, or Firm* — Rimon P.C.

(57) ABSTRACT

This culture device comprises: a duct having an inner wall surface which faces a culture space, and a mounting surface which faces the portion to be mounted to of the inner surface, the mounting surface being mounted to the portion to be mounted to, and an air passage being formed with the inner wall surface; and a microbial light source provided within the passage. A protrusion which comes into close contact with the mounting surface, and which protrudes towards the mounting surface, is formed on the portion to be mounted to, or a protrusion which comes into close contact with the portion to be mounted to and which protrudes towards the portion to be mounted to is formed on the mounting surface.

4 Claims, 3 Drawing Sheets

(56) References Cited

FOREIGN PATENT DOCUMENTS

| | | | |
|---|---|---|---|
| JP | 2010007151 | * | 1/2010 |
| JP | 2010007870 | * | 1/2010 |
| JP | 2017-175944 A | | 10/2017 |
| WO | 2012/140854 A1 | | 10/2012 |
| WO | 2017/169850 A1 | | 10/2017 |

OTHER PUBLICATIONS

International Search Report and Written Opinion issued in International Patent Application No. PCT/JP2019/031921, dated Nov. 12, 2019; with partial English translation.

* cited by examiner

CULTURE DEVICE

CROSS-REFERENCE OF RELATED APPLICATIONS

This application a Continuation of International Patent Application No. PCT/JP2019/031921, filed on Aug. 14, 2019, which in turn claims the benefit of Japanese Application No. 2018-166647, filed on Sep. 6, 2018, the entire disclosures of which Applications are incorporated by reference herein.

TECHNICAL FIELD

The present invention relates to a culture apparatus.

BACKGROUND ART

Conventionally, in a culture apparatus, a duct forming a gas passage for air is disposed in a culture chamber, and an ultraviolet lamp is disposed in the duct. Ultraviolet light irradiation from this ultraviolet lamp sterilizes air flowing in the culture chamber and water in a humidification tray (hereinafter, referred to as "humidification water") installed below the duct (see e.g., Patent Literature (hereinafter referred to as "PTL") 1).

CITATION LIST

Patent Literature

PTL 1
Japanese Patent Application Laid-Open No. 2017-175944

SUMMARY OF INVENTION

Technical Problem

It should be noted here that, when ultraviolet light leaks from inside the duct, the ultraviolet light leaking from the duct affects the culture of cells, microorganisms, and/or the like. Therefore, a culture apparatus in which ultraviolet light leaks from inside the duct is regarded as a nonconforming product and cannot be shipped.

The duct is fixed to the rear-wall inner surface of an inner box at attachment surfaces that are surfaces coming to face the rear-wall inner surface as a result of folding back side edges of the duct inward. Since the inner box is manufactured by welding, the rear wall of the inner box is sometimes curved under the influence of heat during the welding. This curvature sometimes causes a gap partially between the attachment surfaces of the duct and the rear-wall inner surface of the inner box, and the ultraviolet light may thus leak through the gap.

It is desired to reduce the loss in manufacturing by preventing such leakage of ultraviolet light.

The present invention is devised in view of such a desire, and aims to provide a culture apparatus capable of reducing a loss in manufacturing.

Solution to Problem

In order to solve the above-mentioned conventional problem, a culture apparatus of the present invention includes: an inner wall surface facing a culture space; a duct that includes an attachment surface facing an attachment target portion of the inner wall surface, the attachment surface being attached to the attachment target portion, the duct and the inner wall surface forming a passage for air in between; and a light source for sterilization that is disposed in the passage, in which a protrusion protruding toward the attachment surface and making close contact with the attachment surface is formed on the attachment target portion, or a protrusion protruding toward the attachment target portion and making close contact with the attachment target portion is formed on the attachment surface the attachment surface is bent in a width direction, and a leading end of the attachment surface is pressed against the attachment target portion.

Advantageous Effects of Invention

According to the present invention, it is possible to reduce the loss in manufacturing.

DESCRIPTION OF EMBODIMENTS

Figure 1:
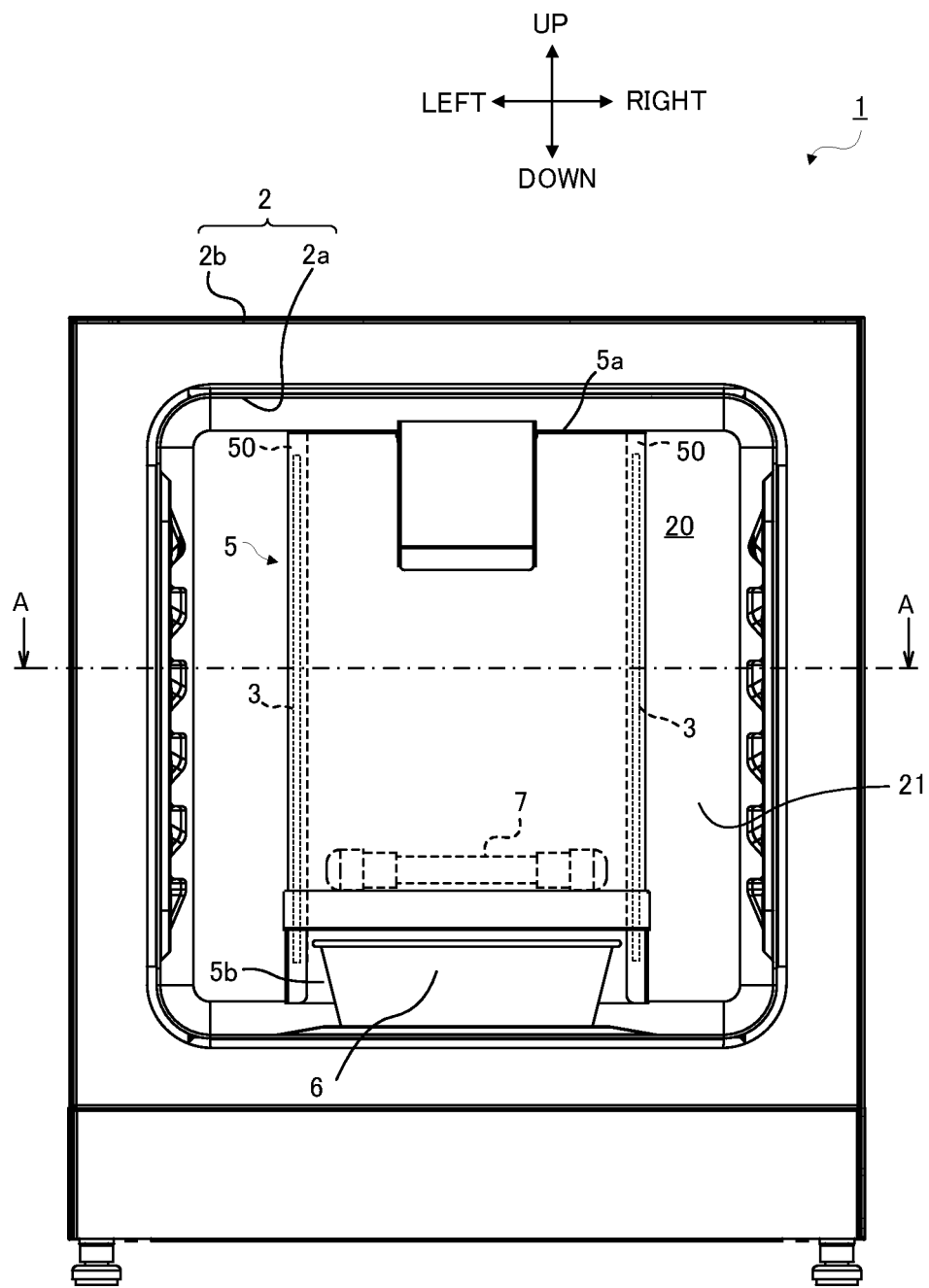
FIG. 1 is a front view illustrating a culture apparatus of an embodiment of the present invention in a state in which an outer door and an inner door are removed.

Hereinafter, a culture apparatus according to an embodiment of the present invention will be described with reference to the accompanying drawings. The following embodiments are merely illustrative, and various modifications and/or applications of techniques which are not specified in the following embodiments are not excluded. In addition, the configurations of the embodiments can be variously modified and implemented without departing from the spirit thereof. Further, the configurations of the embodiments can be selected as necessary, or can be appropriately combined.

In the following description, the side of the culture apparatus which the user faces during usage of the culture apparatus (the side with below-described opening 21 of culture space 20) is referred to as "front" and the side opposite to the front is referred to as "rear." In addition, the left and right are defined with reference to the case of viewing from the front to the rear. In addition, both the left and right directions are collectively referred to as a width direction.

Note that, in all the figures for explaining the embodiments, the same elements are denoted by the same reference numerals in principle, and the description thereof may be omitted.

1. Configuration

Figure 2:
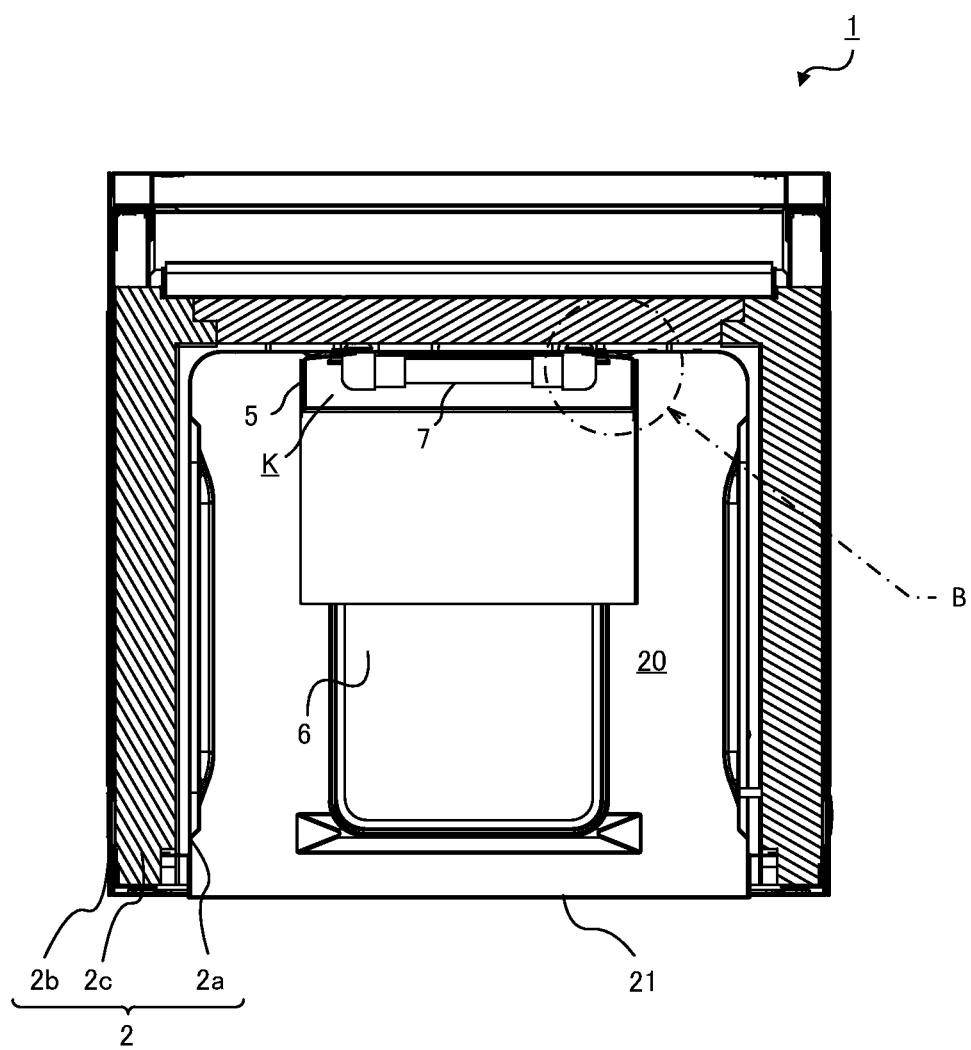
FIG. 2 is a cross-sectional view taken along line A-A in FIG. 1 as seen in the direction of arrows that illustrates a configuration of the culture apparatus of an embodiment of the present invention.
Figure 3:
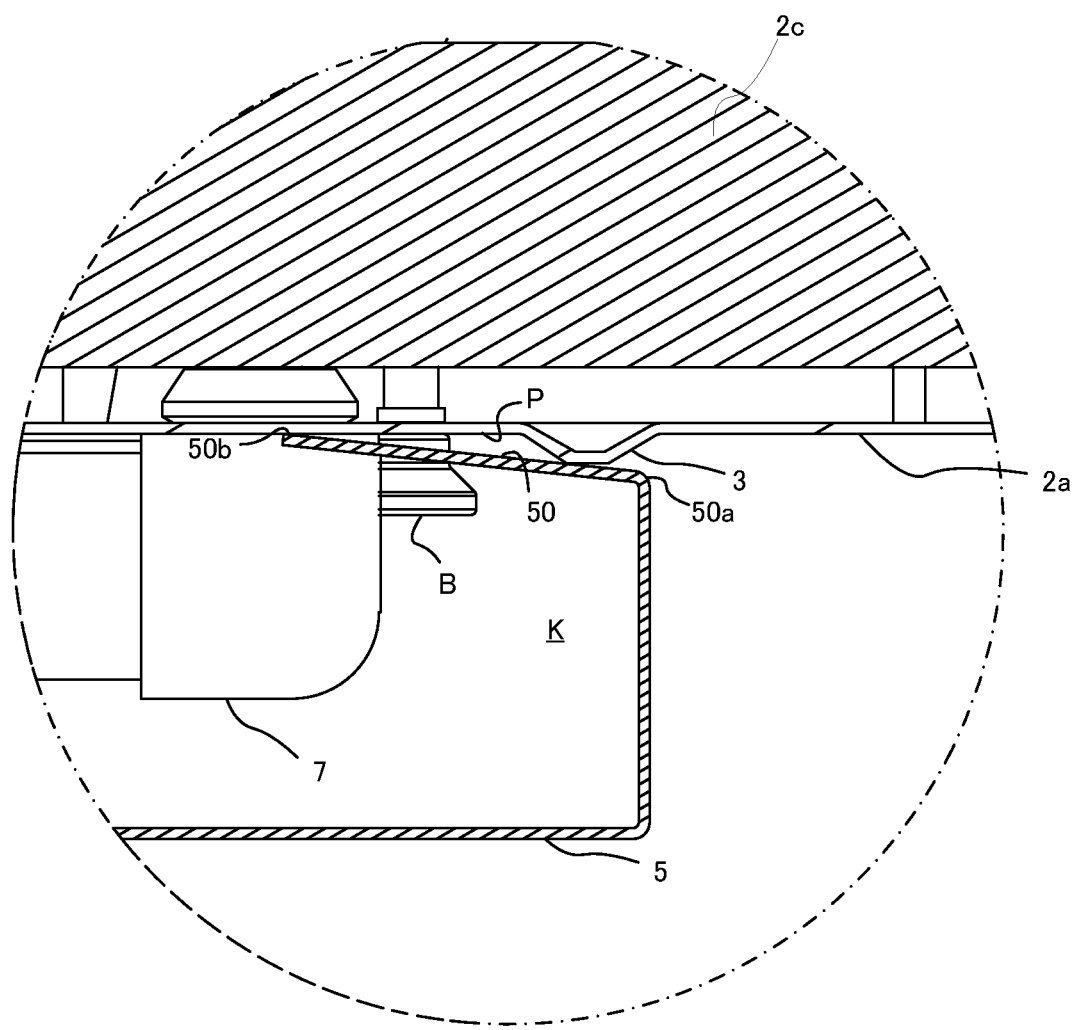
FIG. 3 is an enlarged view of part B in FIG. 2 illustrating a configuration of a principal part of the culture apparatus of an embodiment of the present invention.

Culture apparatus 1 in the present embodiment will be described with reference to FIGS. 1 to 3. FIG. 1 is a front view illustrating a culture apparatus of an embodiment of the present invention in a state in which an outer door and an inner door are removed. FIG. 2 is a cross-sectional view taken along line A-A in FIG. 1 as seen in the direction of arrows that illustrates a configuration of the culture apparatus of an embodiment of the present invention. FIG. 3 is an enlarged view of part B in FIG. 2 illustrating a configuration of a principal part of the culture apparatus of an embodiment of the present invention.

Culture apparatus 1 is an apparatus for growing a culture such as a cell or a microorganism. Culture apparatus 1 is configured to include substantially box-shaped heat insulation box 2 having culture space 20 formed inside and opening 21 formed in the front surface, an outer door (not illustrated) and an inner door (not illustrated) for opening and closing opening 21.

In order to achieve an appropriate environment for culturing cells, microorganisms, and the like, culture space 20 is controlled such that the temperature, humidity, and $CO_2$ concentration are maintained within respective appropriate ranges.

Heat insulation box 2 includes substantially box-shaped inner box 2a having culture space 20 formed inside, substantially box-shaped outer box 2b that covers the outside of inner box 2a, and heat insulation material 2c disposed between inner box 2a and outer box 2b.

In culture space 20, duct 5 extending vertically (in the first direction) is disposed on the rear-wall inner surface (inner wall surface) of inner box 2a. Passage K for air containing $CO_2$ and the like is formed inside duct 5, and a circulation blower (not illustrated) is installed in passage K. By operating the circulation blower, forced circulation of air is performed; the air containing $CO_2$ and the like in culture space 20 is sucked from suction port 5a formed in an upper portion of duct 5, and is blown out to culture space 20 from blow-out port 5b formed in a lower portion of duct 5. Further, a $CO_2$ sensor for detecting $CO_2$ concentration in the air flowing through passage K (not illustrated) is installed in duct 5.

Further, ultraviolet lamp 7 is installed in duct 5.

In addition, humidification tray 6 for storing humidification water is installed between the lower portion of duct 5 and the bottom wall of inner box 2a. Humidification tray 6 is heated by a heater wire (not illustrated) disposed on the bottom wall of inner box 2a, whereby the water stored in humidification tray 6 evaporates.

Ultraviolet lamp 7 in duct 5 described above sterilizes the air in duct 5 and thus the air in culture space 20 accordingly, and the humidification water in humidification tray 6 below duct 5.

As illustrated in FIGS. 1 and 3, in duct 5, attachment surfaces 50 bent in the width direction are formed. In the present embodiment, each of attachment surfaces 50 is bent inward (i.e., toward passage K), but may be bent outward. Further, attachment surfaces 50 are inclined with respect to respective attachment target portions P of the rear-wall inner surface of inner box 2a to which attachment surfaces 50 are attached. Attachment surfaces 50 are inclined such that leading ends 50b are closer to attachment target portions P than bent portions 50a are to the attachment target portions P. That is, attachment surfaces 50 are inclined to be closer to attachment target portions P toward leading ends 50b.

Further, protrusions are formed on respective attachment target portions P of the rear-wall inner surface of inner box 2a. In FIGS. 2 and 3, protruding strips 3 extending vertically are formed as the protrusions on respective attachment target portions P of the rear-wall inner surface of inner box 2a.

In a state where each of attachment surfaces 50 of duct 5 is, at its portion closer to bent portion 50a, in contact with protruding strip 3, attachment surfaces 50 is fixed to inner box 2a by bolts B at portions of the duct closer to the widthwise middle of the rear-wall inner surface than to protruding strip 3.

2. Effects (1) Protruding strips 3 protruding toward attachment surfaces 50 of duct 5 are formed on respective attachment target portions P of the rear-wall inner surface of inner box 2a. Even when attachment target portions P are curved so that the distance between attachment target portions P and attachment surfaces 50 of duct 5 is different between locations, protruding strips 3 formed on attachment target portions P compensate this difference, and respective attachment target portions P of inner box 2a are thus in stable close contact with attachment surfaces 50 of duct 5. Therefore, it is possible to prevent formation of a gap between duct 5 and inner box 2a, so as to reduce the leakage of ultraviolet light from inside duct 5. It is thus possible to reduce the loss of culture apparatus 1 in manufacturing.

(2) Attachment surfaces 50 are inclined to be closer to attachment target portions P toward leading ends 50b, and are in contact with protruding strips 3 on the side of bent portions 50a. For this reason, in a state of being attached to inner box 2a by bolts B, leading ends 50b of attachment surfaces 50 are easily pressed against attachment target portions P. Therefore, formation of a gap between duct 5 and inner box 2a is further prevented, and the leakage of ultraviolet light from inside duct 5 can be effectively reduced. It is thus possible to further reduce the loss in manufacturing.

(3) Protruding strips 3 are shaped to extend along the extending direction of duct 5, and it is thus possible to reduce the leakage of ultraviolet light from inside duct 5 over the extending direction of duct 5 (i.e., the longitudinal direction), so as to further reduce the loss in manufacturing. Further, since protruding strips 3 are shaped to extend along the extending direction of duct 5, it is possible to reduce the curvature of attachment target portions P of inner box 2a.

3. Modifications

Instead of forming protruding strips 3 on attachment target portions P, protruding strips protruding toward attachment target portions P and making close contact with attachment target portions P may be formed on attachment surfaces 50. This configuration also reduces formation of a gap between duct 5 and inner box 2a, to make it possible to reduce the leakage of ultraviolet light from inside duct 5, so as to reduce the loss of culture apparatus 1 in manufacturing.

The disclosure of Japanese Patent Application No. 2018-166647, filed on Sep. 6, 2018, including the specification, claims, drawings and abstract is incorporated herein by reference in its entirety.

INDUSTRIAL APPLICABILITY

The present invention can provide a culture apparatus capable of reducing a loss in manufacturing. Therefore, its industrial applicability is enormous.

REFERENCE SIGNS LIST

1 Culture apparatus
2 Heat insulation box
2a Inner box
2b Outer box
2c Heat insulation material
3 Protruding strip
5 Duct
5a Suction port 5b Blow-out port
6 Humidification tray
7 Ultraviolet lamp
20 Culture space
21 Opening
50 Side edge (attachment surface)
50a Bent portion
50b Leading end
B Bolt
K Passage
P Attachment target portion

The invention claimed is:

1. A culture apparatus, comprising:
a rear-wall inner surface facing a culture space;
a duct that extends in a first direction and comprises attachment surfaces each facing an attachment target portion, which is a part of the rear-wall inner surface, the attachment surfaces each being attached to the attachment target portion, the duct and the rear-wall inner surface forming a passage for air in between so that the air flows along the first direction; and
a light source for sterilization that is disposed in the passage, wherein:
protrusions each protruding toward a corresponding one of the attachment surfaces and making close contact with the corresponding one of the attachment surfaces are formed on the attachment target portion,
each of the attachment surfaces is bent in a width direction perpendicular to the first direction, and
a leading end of each of the attachment surfaces is pressed against the attachment target portion.

2. The culture apparatus according to claim 1, further comprising:
a bolt that fixes the duct to the rear-wall inner surface between a corresponding one of the protrusions and the leading end of each of the attachment surfaces, wherein each of the attachment surfaces is inclined to be closer to the attachment target protrusions toward the leading end.

3. The culture apparatus according to claim 1, wherein each of the protrusions is a protruding strip extending in the first direction.

4. A culture apparatus, comprising:
a rear-wall inner surface facing a culture space;
a duct that extends in a first direction and comprises attachment surfaces each facing an attachment target portion, which is a part of the rear-wall inner surface, the attachment surfaces each being attached to the attachment target portion, the duct and the rear-wall inner surface forming a passage for air in between so that the air flows along the first direction; and
a light source for sterilization that is disposed in the passage, wherein:
protrusions each protruding toward the attachment target portion and making close contact with the attachment target portion formed on each of the attachment surfaces,
each of the attachment surfaces is bent in a width direction perpendicular to the first direction, and
a leading end of each of the attachment surfaces is pressed against the attachment target portion.

* * * * *